(12) United States Patent
Takeuchi et al.

(10) Patent No.: US 8,378,112 B2
(45) Date of Patent: Feb. 19, 2013

(54) GLYCYRRHETINIC ACID DERIVATIVE AND USE THEREOF

(75) Inventors: Hideyuki Takeuchi, Nagoya (JP); Akio Suzumura, Nagoya (JP)

(73) Assignees: INI Corporation, Aichi (JP); University Corporation Nagoya University, Aichi (JP)

( * ) Notice: Subject to any disclaimer, the term of this patent is extended or adjusted under 35 U.S.C. 154(b) by 0 days.

(21) Appl. No.: 13/054,161

(22) PCT Filed: Jul. 15, 2009

(86) PCT No.: PCT/JP2009/003351
§ 371 (c)(1),
(2), (4) Date: Apr. 6, 2011

(87) PCT Pub. No.: WO2010/007788
PCT Pub. Date: Jan. 21, 2010

(65) Prior Publication Data
US 2011/0190354 A1    Aug. 4, 2011

(30) Foreign Application Priority Data

Jul. 16, 2008  (JP) .................................. 2008-185304

(51) Int. Cl.
*A61K 31/455* (2006.01)
*A61P 25/00* (2006.01)
*C07D 213/80* (2006.01)
(52) U.S. Cl. ........................................ 546/285; 514/356
(58) Field of Classification Search .................. None
See application file for complete search history.

(56) References Cited

PUBLICATIONS

Yoneda et al., Trypsin Inhibiting Action of Glycyrrhetinic Acid Derivatives, 48(2) Nippon Nogei Kagaku Kaishi 147-9 (1974) (CAS Abstract).*
Richard B. Silverman, The Organic Chemistry of Drug Design and Drug Action, Chapter 2: Drug Discovery, Design, and Development, Academic Press, p. 5-51 (1992).*
Berge et al., Pharmaceutical Salts, 66(1) J. Pharma Sci. 1-19 (Jan. 1977).*

* cited by examiner

*Primary Examiner* — Nizal Chandrakumar
*Assistant Examiner* — Timothy R Rozof
(74) *Attorney, Agent, or Firm* — Konomi Takeshita

(57) ABSTRACT

Disclosed is a gap junction inhibitor which is more practically useful compared with carbenoxolone. Also disclosed is a novel glycyrrhetinic acid derivative. The glycyrrhetinic acid derivative is represented by general formula (1) or (2).

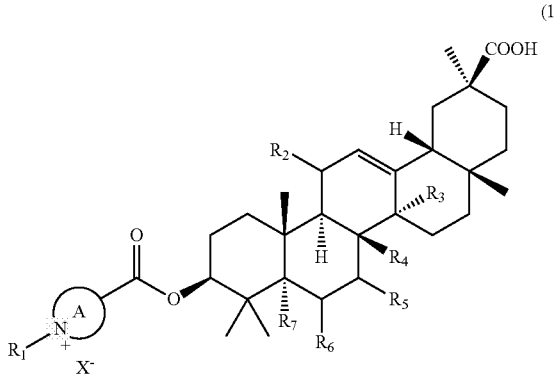

(1)

23 Claims, 16 Drawing Sheets

GLYCYRRHETINIC ACID DERIVATIVE AND USE THEREOF

CROSS REFERENCE TO RELATED APPLICATIONS

This application claims priority under 35 U.S.C. 119 based upon the Japanese Patent Application No. 2008-185304, filed on Jul. 16, 2008. The entire disclosure of the aforesaid application is incorporated herein by reference.

FIELD OF THE INVENTION

The present invention relates to a novel glycyrrhetinic acid derivative or a pharmaceutically acceptable salt thereof, a pharmaceutical composition containing the same as an active ingredient, and a method for treating neurological disorders using said glycyrrhetinic acid derivative or a pharmaceutically acceptable salt thereof.

BACKGROUND OF THE INVENTION

A gap junction is known as a cell-to-cell contact site on a cell surface. The present inventors had discovered that carbenoxolone, a glycyrrhetinic acid derivative, which is a gap junction inhibitor, inhibits the release of excess glutamate from activated microglia and established that a gap junction inhibitor can be used for treating nervous system diseases. (Patent reference 1)

Furthermore, a gap junction is known to be involved in a variety of transmissions of stimulation such that novel junction inhibitors are useful for various research applications.
Patent reference 1: International publication WO 2007/No. 088712 pamphlet.

SUMMARY OF THE INVENTION

Although carbenoxolone is effective as a gap junction inhibitor, its systemic distribution led to a concern that a mineralocorticoid action in the kidney might cause hypokalemia, edema, and the like. An object of the present invention is to provide a novel glycyrrhetinic acid derivative which has a more practical gap junction inhibitory action than does carbenoxolone.

The present inventors' studies on glycyrrhetinic acid derivatives of carbenoxolone led to the finding that the derivatives obtained by replacing the 4-hydroxy-4oxobutanoyl group at position 10, the site connected to the glycoside of the glycyrrhetinic acid skeleton, with the addition of a heterocyclic salt containing 1 to 5 hetero-atoms selected from an oxygen, sulfur, and nitrogen atom, via a linking group (carbonyloxy group), or a pharmaceutically acceptable salt thereof, has, through its inhibitory action on gap junction, a strong glutamate release inhibitory effect on activated microglia and neuronal cell death inhibitory activity and also has a good survival extension effect when administered to amyotrophic lateral sclerosis (ALS) model mice, which has led to the completion of the present invention.

That is, the present invention provides a glycyrrhetinic acid derivative represented by the following general formula (1) or (2) and a pharmaceutically acceptable salt thereof. (in the formula, ring A represents a heterocyclic ring which may also have a substituent group in addition to R1; R1 a linear or branched alkyl group having 1 to 6 carbon atoms which may have a substituent; R2 a hydroxyl or carbonyl group; R3 a hydrogen atom, a hydroxyl group or a linear or branched alkyl group having 1 to 4 carbon atoms; R4 a hydrogen atom, a hydroxyl group, or a linear or branched alkyl group having 1 to 4 carbon atoms; R5 a hydrogen atom, a hydroxyl, a carbonyl group (O=) or a linear or branched alkyl group having 1 to 4 carbon atoms; R6 a hydrogen atom, a hydroxyl, a carbonyl group (O=) or a linear or branched alkyl group having 1 to 4 carbon atoms, or a halogen atom; R7 a hydrogen atom or a hydroxyl group; R8 a hydrogen atom, a hydroxyl group or a halogen atom; and $X^-$ represents an anion.)

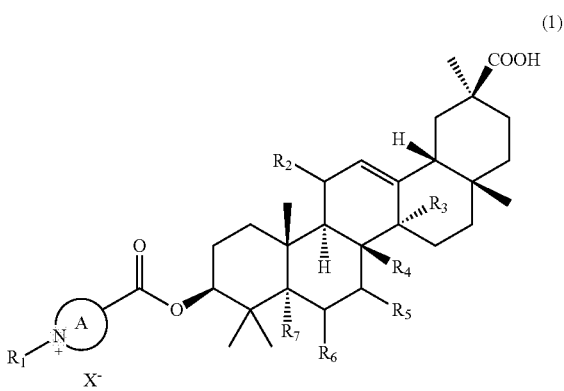

(1)

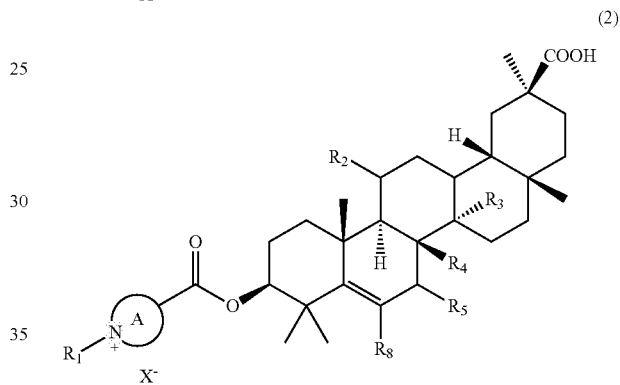

(2)

In said general formula (1) or (2), Ring A is preferably one of pyridine, quinoline, isoquinoline, imidazole, oxazole, thiazole, benzoxazole, 2,1-benzisooxazole, benzthiazole or 2,1-benzisothiazole, particularly pyridine.

Moreover, Ring A preferably possesses only R1 as a substituent group.

Further, in said general formula (1) or (2), R1 may be an alkyl group having 1 to 4 carbon atoms. Furthermore, R1 may represent a methyl group in said formula (1) or (2).

Specific examples of compounds represented by general formula (1) or (2) include glycyrrhetinic acid derivatives represented by the following chemical formula:

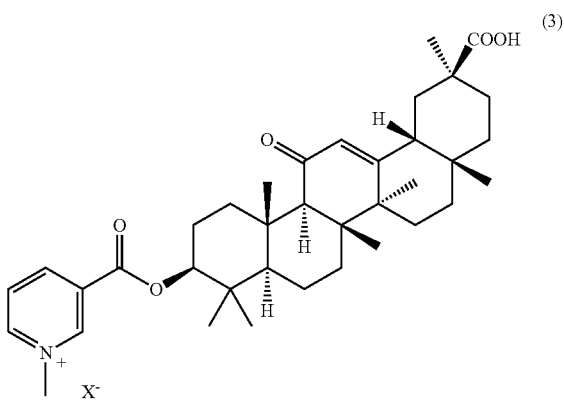

(3)

The present invention provides a pharmaceutical composition containing as an active ingredient, said glycyrrhetinic acid derivatives or a pharmaceutically acceptable salt thereof. The pharmaceutical composition of the present invention can be used for preventing or treating a neurological disease.

Moreover, the present invention provides a method of treating a mammal afflicted with a neurological disease, said method comprising the step of making available a glycyrrhetinic acid derivative represented by general formula (1) or (2) and pharmaceutically acceptable salts thereof and the step of administering to said mammal a therapeutically effective amount of said made-available glycyrrhetinic acid derivatives and pharmaceutically acceptable salts thereof. The novel method with such constitution is provided for treating mammals afflicted with a neurological disease.

It is preferred in said method that said mammal is a human and said administering step is performed orally.

Furthermore, in the compounds represented by said general formula (1) or (2) which are used in said therapeutic method, the Ring A is preferably one of pyridine, quinoline, isoquinoline, imidazole, oxazole, thiazole, benzoxazole, 2,1-benzisooxazole, benzthiazole or 2,1-benzisothiazole, particularly pyridine. Moreover, the Ring A may have only R1 as a substituent group. Further, in said general formula (1) or (2), R1 may be an alkyl group having 1 to 4 carbon atoms. Furthermore, R1 may represent a methyl group in said formula (1) or (2).

In addition, the glycyrrhetinic acid derivatives represented by said chemical formula (3) can be mentioned as specific examples of the compounds represented by said general formula (1) or (2), used in said treatment method.

DETAILED DESCRIPTION OF THE INVENTION

Figure 1:
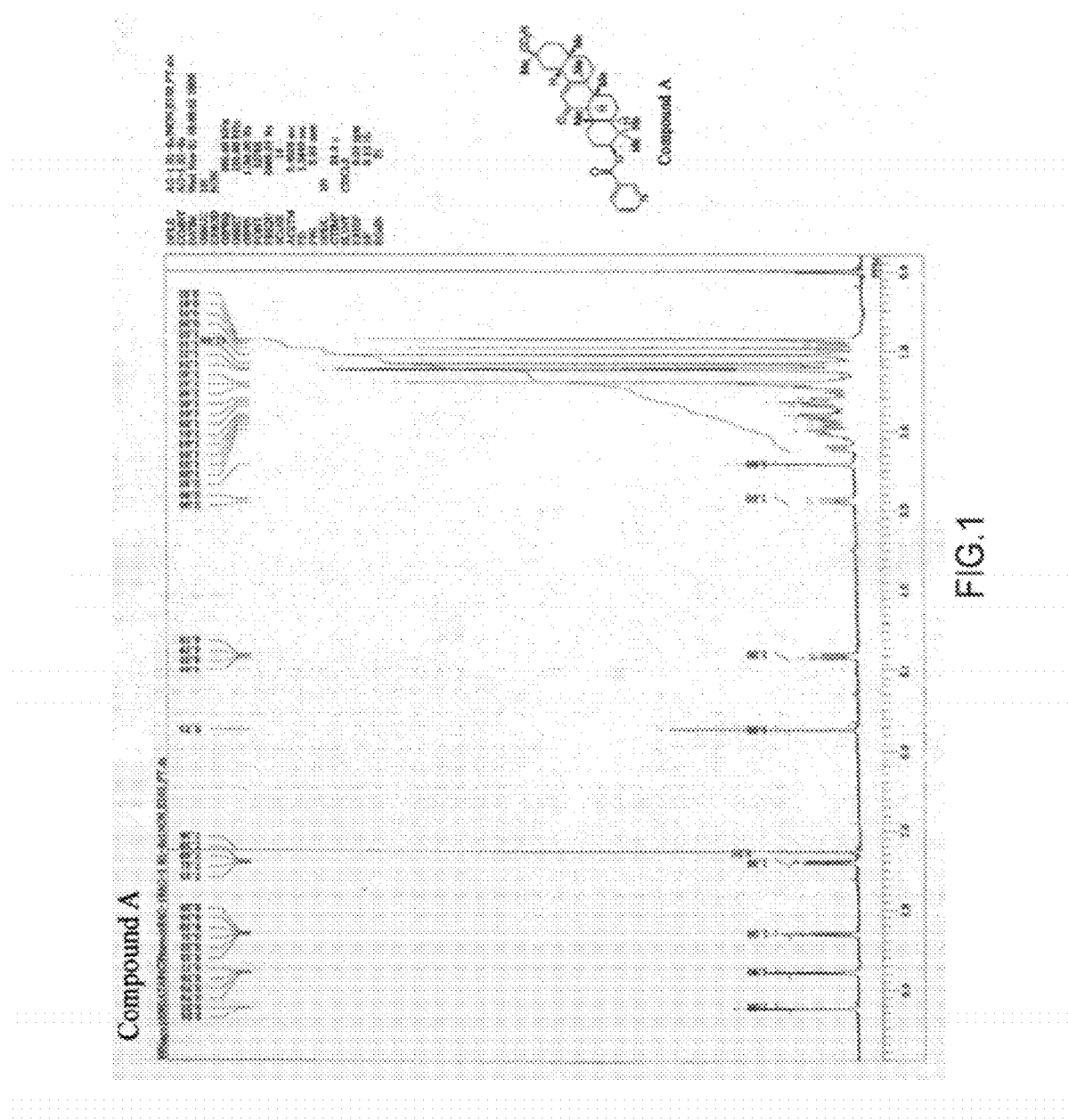
FIG. 1 is a diagram showing the NMR spectrum of Compound A synthesized in Example 1.

The novel glycyrrhetinic acid derivative of the present invention is useful for inhibiting neuronal cell death originating from excessive glutamate production and release by activated microglia, thereby preventing or treating a neurodegenerative disease and the like in which neuronal cell death occurs. Moreover, the novel glycyrrhetinic acid derivatives of the present invention or pharmaceutically acceptable salts thereof have been shown to exhibit a good cell death inhibitory effect on neuronal cells at the cell level and a good survival extension effect in ALS model mice which were intraperitoneally administered therewith.

The novel glycyrrhetinic acid derivatives of the present invention can be used as gap junction inhibitors in themselves and are useful for improving the disease or conditions which can occur as a result of an increase in gap junctions.

The glycyrrhetinic acid derivative of the present invention will be specifically explained hereinafter.

In the glycyrrhetinic acid derivatives of the present invention, Ring A in the compound represented by the general formula (1) or (2) is a heterocyclic ring which may have, in addition to R1, one to three identical or different substituent groups. Herein, "heterocyclic ring" means a cyclic compound containing 1 to 5 hetero atoms selected from an oxygen, sulfur, and nitrogen atom, preferably pyridine, quinoline, isoquinoline, imidazole, oxazole, thiazole, benzoxazole, 2,1-benzisooxazole, benzthiazole or 2,1-benzisothiazole, more preferably pyridine, quinoline, and isoquinoline. Further, substituent groups which said heterocyclic ring may have are a halogen atom, an alkyl group (said alkyl group may be substituted with a halogen atom and a hydroxyl, alkoxy, amino, monoalkylamino, and dialkylamino group), a hydroxyl group, alkoxy group, amino group (said amino group may be substituted with 1 to 2 groups chosen from alkyl and acyl groups), a cyano, carboxyl, alkoxycarboxyl, alkanoyl, and alkenyl group (which may be substituted with an alkoxy group), and the like.

"Halogen atom" means a fluorine, chlorine, iodine or a bromine atom; "alkyl" means a linear or branched alkyl having 1 to 6 carbon atoms, preferably 1 to 4 carbon atoms; "alkoxy" means a linear or branched alkoxy having 1 to 6 carbon atoms, preferably 1 to 4 carbon atoms; "alkanoyl" means a linear or branched alkanoyl having 1 to 7 carbon atoms, preferably having 2 to 5 carbon atoms; "alkenyl" means a linear or branched alkenyl having 2 to 6 carbon atoms, preferably having 2 to 4 carbon atoms.

Ring A may have only R1 without having such substituent groups. R1 is preferably an unsubstituted alkyl group. Unsubstituted alkyl groups include methyl, ethyl, propyl, iso-propyl, butyl, isobutyl, sec-butyl, tert-butyl, pentyl, isopentyl, neopentyl, tert-pentyl, hexyl, isohexyl, and the like. More preferred alkyl groups are methyl, ethyl, propyl, isopropyl, and butyl; still more preferred are methyl or ethyl; and particular preferred is methyl.

In addition, there is no particular limitation as to the position at which ring A is connected to the glycyrrhetinic acid skeleton. For example, in the case where ring A is pyridine and the substituent group is only R1, the ring may be connected at any position of the ring A (pyridine) to a glycyrrhetinic acid skeleton.

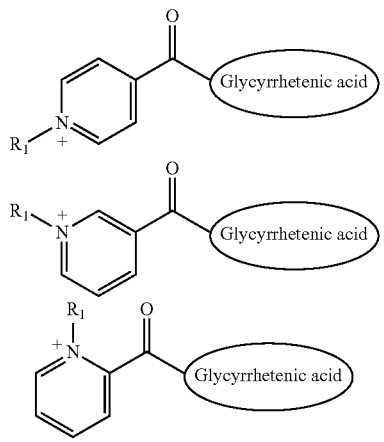

The glycyrrhetinic acid derivative of the present invention may have various substituent groups in the glycyrrhetinic acid skeleton besides Ring A, as long as the effect thereof as a gap junction inhibitor is not adversely affected. Specifically, the R2 to R8 positions in the general formula (1) or (2) may be the following substituents, respectively.

For R2, a carbonyl (O=) or hydroxyl group; for R3 and R4, a hydrogen atom, a hydroxyl or a linear or branched alkyl group having from 1 to 4 carbon atoms; for R5, a hydrogen atom, a hydroxyl, carbonyl (O=), or a linear or branched alkyl group having from 1 to 4 carbon atoms; for R6, a hydrogen atom, a hydroxyl group, carbonyl (O=), a linear or branched alkyl group having from 1 to 4 carbon atoms or a halogen atom; for R7, a hydrogen atom or a hydroxyl group; and for R8, a hydrogen atom, hydroxyl group, or a halogen atom.

More preferred are: for R2, a carbonyl group (O=); for R3, a hydrogen atom, hydroxyl, methyl or ethyl group; and for R4, a hydrogen atom, methyl or ethyl group; for R5, a hydrogen atom, a hydroxyl or carbonyl (O=) group; for R6, a hydrogen atom or a halogen atom; for R7 and R8, a hydrogen atom or a hydroxyl group.

The glycyrrhetinic acid derivatives of the present invention may further have a substituent group, in addition to above R2 to R8 in the glycyrrhetinic acid skeleton beside Ring A. Such substituent group will not be particularly limited as long as the function thereof as a gap junction inhibitor is not adversely affected, said group including such as a halogen atom; an alkyl group (said alkyl group may be substituted with a group selected from a halogen atom, a hydroxyl, alkoxy, amino, monoalkylamino, and dialkyl amino group); a hydroxyl group, an alkoxy group, an amino group (where said amino group may be substituted with one to two groups selected from alkyl and acyl groups); a cyano group; a carboxyl group; an alkoxycarbonyl group; an alkenyl group (which may be substituted with an alkoxy group); and the like. Preferred examples among them are an alkyl group, a hydroxyl group, a halogen atom, and the like.

The compound represented by the following formulas (3) can be preferably used as a glycyrrhetinic acid derivative of the present invention.

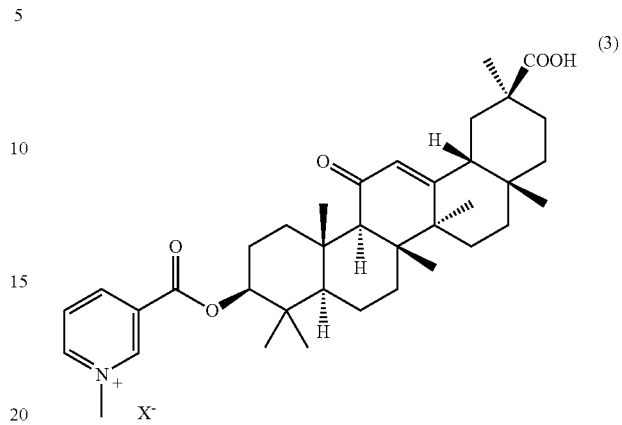

Depending on the substitute group type, the glycyrrhetinic acid derivatives of the present invention will exist as optical isomers (optically active compounds, diastereomers, and the like) or geometric isomers. Therefore, the glycyrrhetinic acid derivatives of the present invention include mixtures of these optical isomers or geometric isomers and those isolated therefrom.

Further, the $X^-$ in the glycyrrhetinic acid derivatives of the present invention include inorganic anions such as chloride ion, bromide ion, iodide ion; and organic anions such as acetate anion, propionate anion, oxalate anion, and succinate anion, and the like. Preferred are inorganic anions such as iodide ion and the like.

Furthermore, the glycyrrhetinic acid derivatives of the present invention also include all of the so-called prodrugs that can be metabolized in vivo to the glycyrrhetinic acid derivatives of the present invention. Listed as groups that form prodrugs with the glycyrrhetinic acid derivatives of the present invention are those groups described in Prog. Med., 5; 2157-2161 (1985) and those described in "Iyakuhin no Kaihatsu" ("Development of Pharmaceuticals"), vol. 7, Bunshi Sekkei ("Molecular Design"), pp. 163-198, a publication in 1990 by Hirokawa Shoten. Specifically these groups are those that can be converted by hydrolysis, solvolysis or under physiological conditions to HOC(=O)— and the like as in the present invention: for OH prodrugs, they include a lower, substitutable alkyl-C(=O)O—; a substitutable aryl-C(=O)O—; ROC(=O)— a substitutable lower alkylene-C(=O)O (where R represents H or a lower alkyl, likewise hereinafter); ROC(=O)— substitutable lower alkenylene-C(=O) O—; ROC(=O)—C(=O)O—; ROS(=O)$_2$— substitutable lower alkenylene-C(=O)O—; phthalidyl-O—; 5-methyl-1,3-dioxolene-2-on-4-yl-methyloxy, and the like.

(The Method of Producing Glycyrrhetinic Acid Derivatives)

The typical method of producing the glycyrrhetinic acid derivatives of the present invention is explained below:

The glycyrrhetinic acid derivatives of the present invention can be produced with the application of various synthetic methods in accordance with the types of the basic skeleton or substituent group thereof. A representative production method is explained by an example for a glycyrrhetinic acid derivative of said general formula (3) where $X^-$ is an iodide ion (I$^-$). A typical production scheme is shown below:

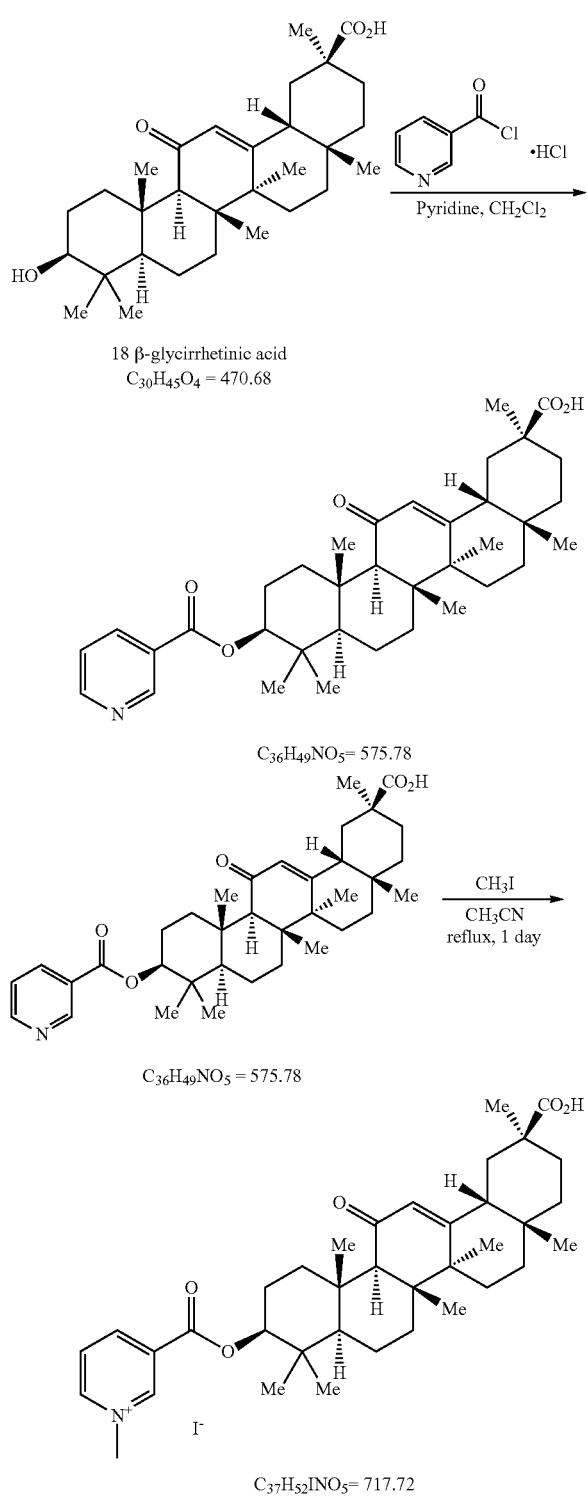

First, 18 β-glycyrrhetinic acid is made available as a starting material. Subsequently, nicotinoyl chloride hydro chloride salt can be reacted with 18βbeta-glycyrrhetinic acid, thereby introducing nicotinate to the hydroxyl group of the 18βbeta-glycyrrhetinic acid followed by attaching an alkyl group to the nitrogen atom of the pyridine ring thereof with methyl iodide or the like.

Typically, the resultant glycyrrhetinic acid derivative of the present invention is produced and isolated, as a pyridinium salt. If obtained as a free base, subjecting it to a salt formation reaction can produce the glycyrrhetinic acid derivative of the present invention.

Further, the raw material compound (starting material) for the glycyrrhetinic acid derivative of the present invention is available from nature or commercially, and also can be produced from a similar skeletal compound by a synthetic method well known in the art.

Thus, the glycyrrhetinic acid derivatives or pharmaceutically acceptable salts thereof are isolated and purified by applying customary chemical operations such as extraction, concentration, distillation, crystallization, filtration, recrystallization, various types of chromatography, and the like. Further, various isomers can be separated, by selecting the appropriate raw material or by making use of differences in physical or chemical properties between the isomers. For example, optical isomers can be separated into stereochemically pure isomers by selecting the appropriate raw material, or by a racemic resolution (for example by a general method of conversion into a diastereomer salt with an optically active acid followed by racemic resolution and the like.)

(Pharmaceutical Composition)

The pharmaceutical composition of the present invention contains, as an active ingredient, a glycyrrhetinic acid derivative of the present invention. The glycyrrhetinic acid derivative of the present invention is offered as a pharmaceutical composition in various types of preparation forms by applying a variety of conventionally used formulas. The pharmaceutical composition of the present invention contains as active ingredients one, two or more, selected from the glycyrrhetinic acid derivatives and pharmaceutically acceptable salts thereof, and can, in addition, contain pharmaceutically acceptable carriers to be prepared in tablets, powdered drugs, granulated agents, granules, encapsulated formulations, pills, syrup agents, injectables, suppositories, ointments, skin patches, and the like, using carriers, excipients, and other additives which are used conventionally in formulation, and it is administered perorally (including sublingual administration) or parenterally.

The formulations, which are pharmaceutical compositions of the present invention) produced by well known methods using additives, such as excipients (for example, organic based excipients, such as sugar derivatives, such as, lactose, sucrose, glucose, mannitol and sorbitol; starch derivatives, such as corn starch, potato starch, a starch and dextrin; cellulose derivatives such as crystalline cellulose; gum arabic; dextran; and pullulan; and inorganic based excipients such as silicate derivatives such as light anhydrous silicic acid, synthetic aluminum silicate, calcium silicate and magnesium meta-silicate aluminate; phosphates such as calcium hydrogen phosphate; carbonates such as calcium carbonate; and sulfates such as calcium sulfate can be listed); lubricants (for example, stearic acid and metal stearate salts such as calcium stearate and magnesium stearate; talc; colloidal silica, veegum; waxes such as whale wax; boric acid; adipic acid; sulfates such as sodium sulfate; glycol; fumaric acid; sodium benzoate; DL leucine; fatty acid sodium salts; lauryl sulfates such as sodium lauryl sulfate and magnesium lauryl sulfate; silicic acids such as anhydrous silicic acid, and silicic acid hydrate; and, the above-mentioned starch derivative can be listed); binders (for example, hydroxypropyl cellulose, hydroxypropyl methyl cellulose, polyvinylpyrrolidone, macrogol, and, compounds similar to the above excipients can be listed); disintegrants (for example, cellulose derivatives such as, low degree of substituent hydroxypropyl cellulose, carboxymethyl cellulose, calcium carboxymethyl cellulose, internally-crosslinked sodium carboxymethyl cellulose; chemically modified starch and celluloses such as carboxymethyl starch, sodium carboxymethyl starch and crosslinked polyvinylpyrrolidone can be listed); stabilizers (parahydroxy benzoates such as methylparaben and propylparaben; alcohols such as chlorobutanol, benzyl alcohol and phenylethyl alcohol; benzalkonium chloride; phenols such as phenol and cresol; thimerosal; dehydroacetic acid; and, sorbic acid can be listed); flavoring and perfuming agents (for example, commonly used sweeteners, acidulants, flavors, and the like can be listed); diluents and the like The dosage of the glycyrrhetinic acid derivative of the present invention or a pharmaceutically acceptable salt thereof will differ differs depending on the symptoms, age, and the like, and is suitably determined in each case. For example, for a peroral administration, it can be administered to an adult once or several times a day at a per administration daily lower limit of 0.1 mg (preferably, 1 mg) and upper limit of 1000 mg (preferably 500 mg); and for an intravenous administration at a per administration daily lower limit of 0.01 mg (preferably, 0.1 mg) and upper limit of 500 mg (preferably 200 mg).

The pharmaceutical composition of the present invention can be used for preventing, treating, and improving the disease or symptoms caused by an increase in gap junctions, or preventing, treating, and improving the disease or symptoms for which an inhibition of gap junction is effective. For example, it is preferred to be used as a neuronal cell death inhibitor for glutamate-induced excitotoxic neurodegeneration. In addition, it is preferably used for preventing and treating nervous system diseases which involve neuronal cell death due to such excitotoxic neurodegeneration for humans and nonhuman animals such as domesticated animals and pets. The nervous system diseases include, for example, ischemic disorders, inflammatory neurological diseases, and neurodegenerative diseases.

Listed for the ischemic disorders are, cerebral stroke, brain hemorrhage, cerebral infarction and cerebrovascular dementia. Listed for the inflammatory neurological disorder are central nervous system inflammatory neurological disorder such as Alzheimer's disease, post-encephalitic syndromes, acute disseminated encephalomyelitis, bacterial meningitis, tuberculous meningitis, fungal meningitis, viral meningitis and post-vaccinal meningitis and the like. Listed for the neurodegenerative disease are, for example, Alzheimer's disease (also an inflammatory neurological disease), head injury, cerebral palsy, Huntington's disease, Pick's disease, Down's syndrome, Parkinson's disease, AIDS encephalopathy, multiple system atrophy, multiple sclerosis (also an inflammatory neurological disease) amyotrophic lateral sclerosis, spinocerebellar degeneration and the like.

In addition, the pharmaceutical composition of the present invention does not bar using it with other pharmaceuticals which are effective for neurodegenerative diseases and the like. For example, the combined use thereof with various pharmaceuticals used for ischemic disorders, inflammatory neurological diseases, and neurodegenerative diseases is not barred. For example, for the Alzheimer's disease, they are donepezil, memantine, rivastigmine, galantamine, and the like; for the multiple sclerosis, they are interferon, glucocorticosteroid, anticonvulsant drugs, an immunosuppressant and the like; for the Parkinson's disease, they are dopamine, anticholinergic agent, a dopamine release inhibitor (amantadine); dopamine receptor stimulant (ergot or non-ergot alkaloid); dopamine breakdown inhibitor (Selegilene) and the like; for the spinocerebellar degeneration, they are protirelin tartrate, taltirelin hydrate; for the amyotrophic lateral sclerosis, they are riluzole and the like.

The present invention is explained specifically hereinafter with examples, but the invention is not limited to these examples.

EXAMPLE 1

(Synthesis of the Glycyrrhetinic Acid Derivatives of the Present Invention)

The glycyrrhetinic acid derivative (henceforth also called Compound B) in which $X^-$ in Formula (3) is iodide ion ($I^-$) was synthesized according to the following scheme:

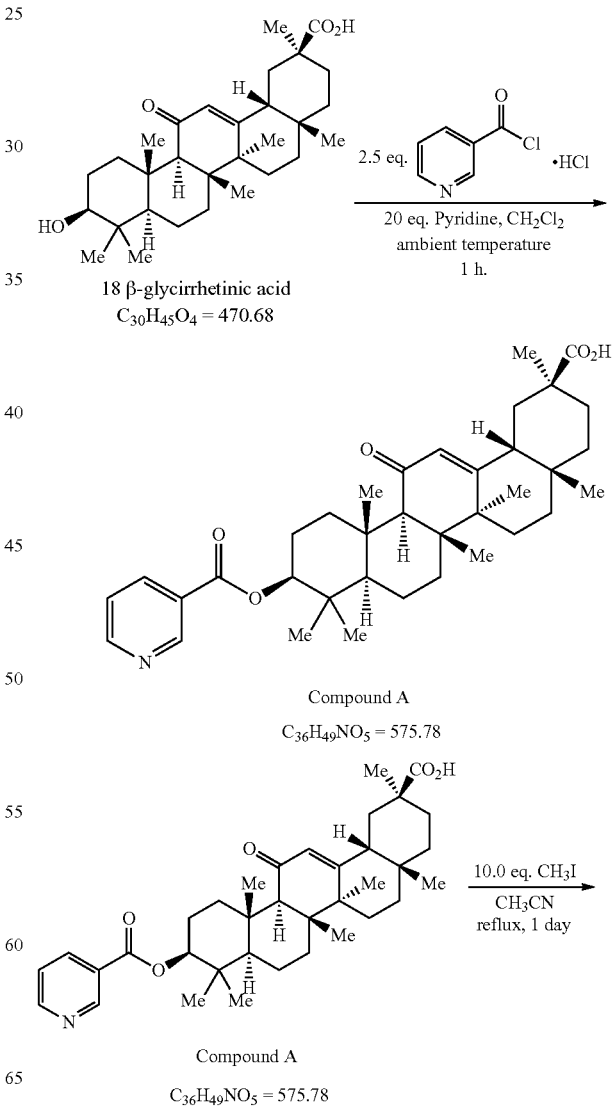

18 β-glycirrhetinic acid
$C_{30}H_{45}O_4 = 470.68$

Compound A
$C_{36}H_{49}NO_5 = 575.78$

Compound A
$C_{36}H_{49}NO_5 = 575.78$

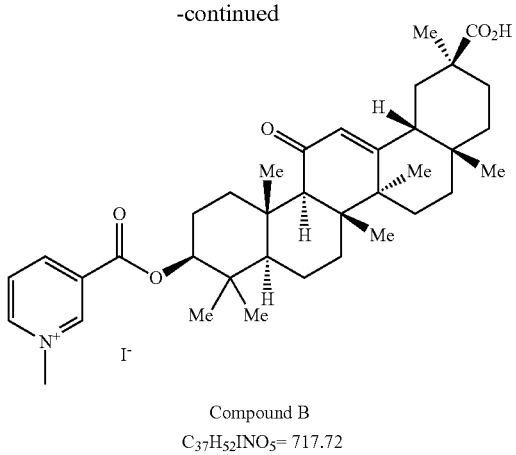

Compound B
$C_{37}H_{52}INO_5$ = 717.72

Figure 2:
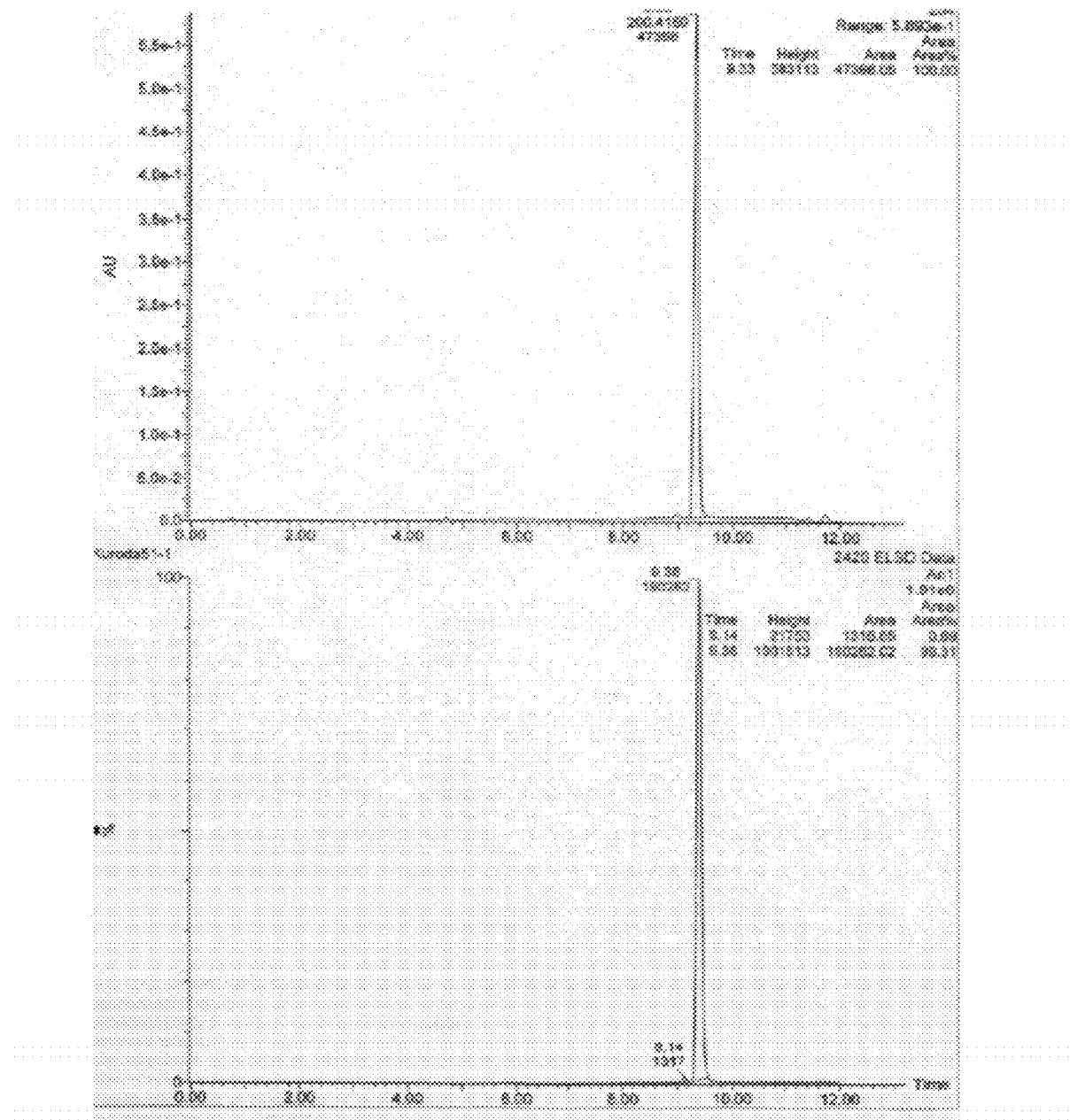
FIG. 2 is a diagram showing the LC-MS spectrum of compound A synthesized in Example 1.

Namely, under an argon atmosphere, nicotinoyl chloride hydrochloride (38.2 g, 214.5 mmol, 2.5 equivalents) and dichloromethane (700 ml) were placed in a 2.0 L 5-necked flask; and pyridine (138.7 ml, 1.716 moles, 20 equivalents) was added dropwise thereto with stirring at an internal temperature of 23° C. After the end of the dropwise addition, 18β-glycyrrhetinic acid (35.0 g, 85.8 moles, 1.0 equivalent) was added to the reaction solution and was stirred at an internal temperature of 23° C. for one hour. After the disappearance of the raw material was confirmed using TLC (thin layer chromatography), water (800 ml) was added, followed by further stirring for one hour. The organic layer was collected and dried over anhydrous sodium sulfate (200 g); and the organic solvent was evaporated off by a rotary evaporator. The resultant concentrated residue was purified by silica gel column chromatography (silica gel 1.0 kg; elutant solvents: dichloromethane, 1%, 2%, and 5% methanol-containing dichloromethane). A fraction containing the goal product was collected and concentrated; the resultant crude refined product (a white powder) was mixed with methanol (300 ml) and heated and refluxed for 30 minutes, and gradually cooled with stirring. The resultant precipitate was collected by filtration, washed with methanol, and dried at reduced pressure, yielding Compound A (Yield 33.3 g, percent yield 67.4%; a white powder, Rf (a relative value of the distance traveled by the product relative to the distance traveled by the solvent front) of 0.5 (dichloromethane: methanol=9:1, UV 254 nm). The NMR spectrum of the resultant compound A is shown in FIG. 1. Its LC-MS spectrum is shown in a FIG. 2.

Figure 3:
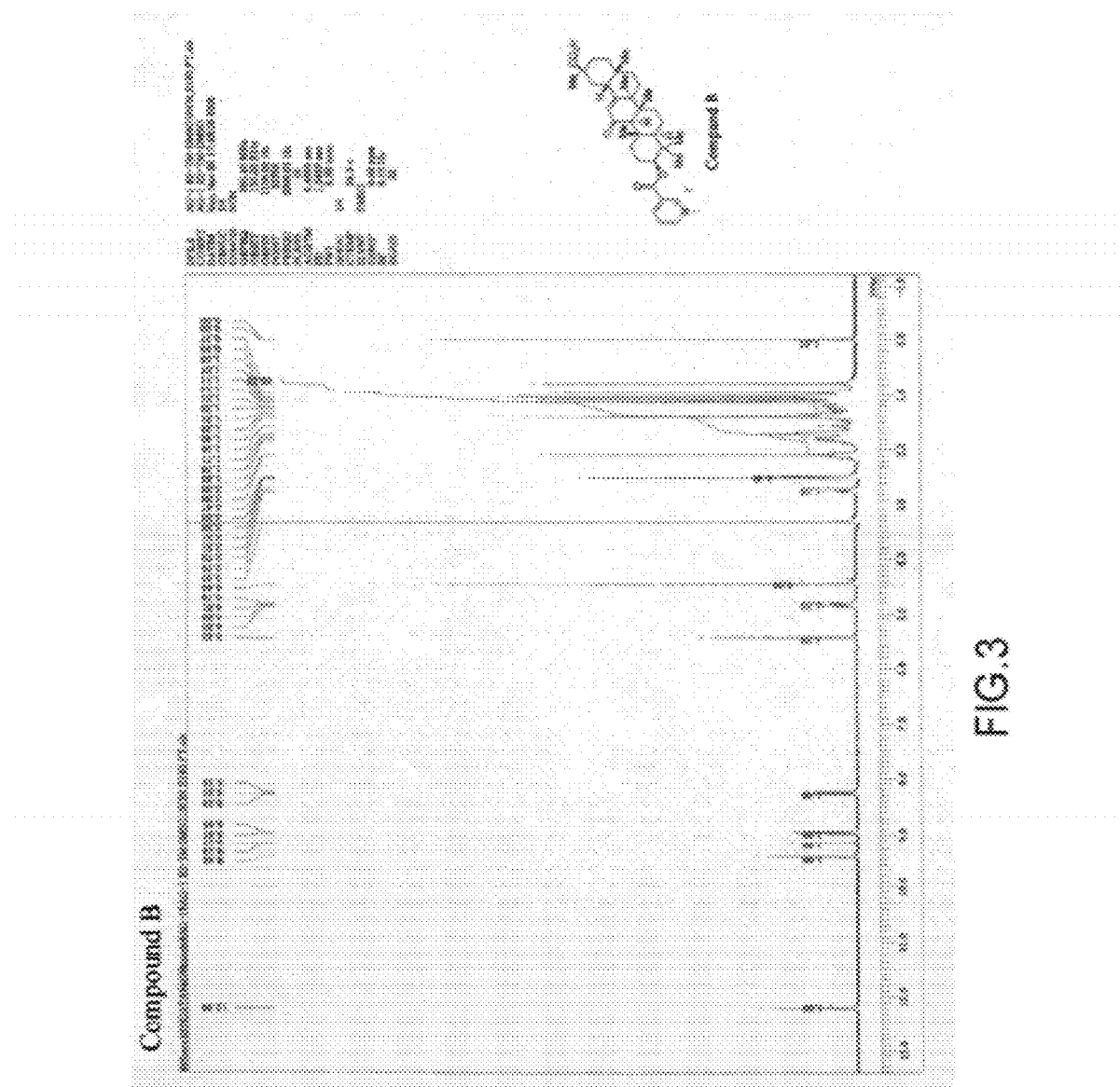
FIG. 3 is a diagram showing the NMR spectrum of the compound B synthesized in Example 1.
Figure 4:
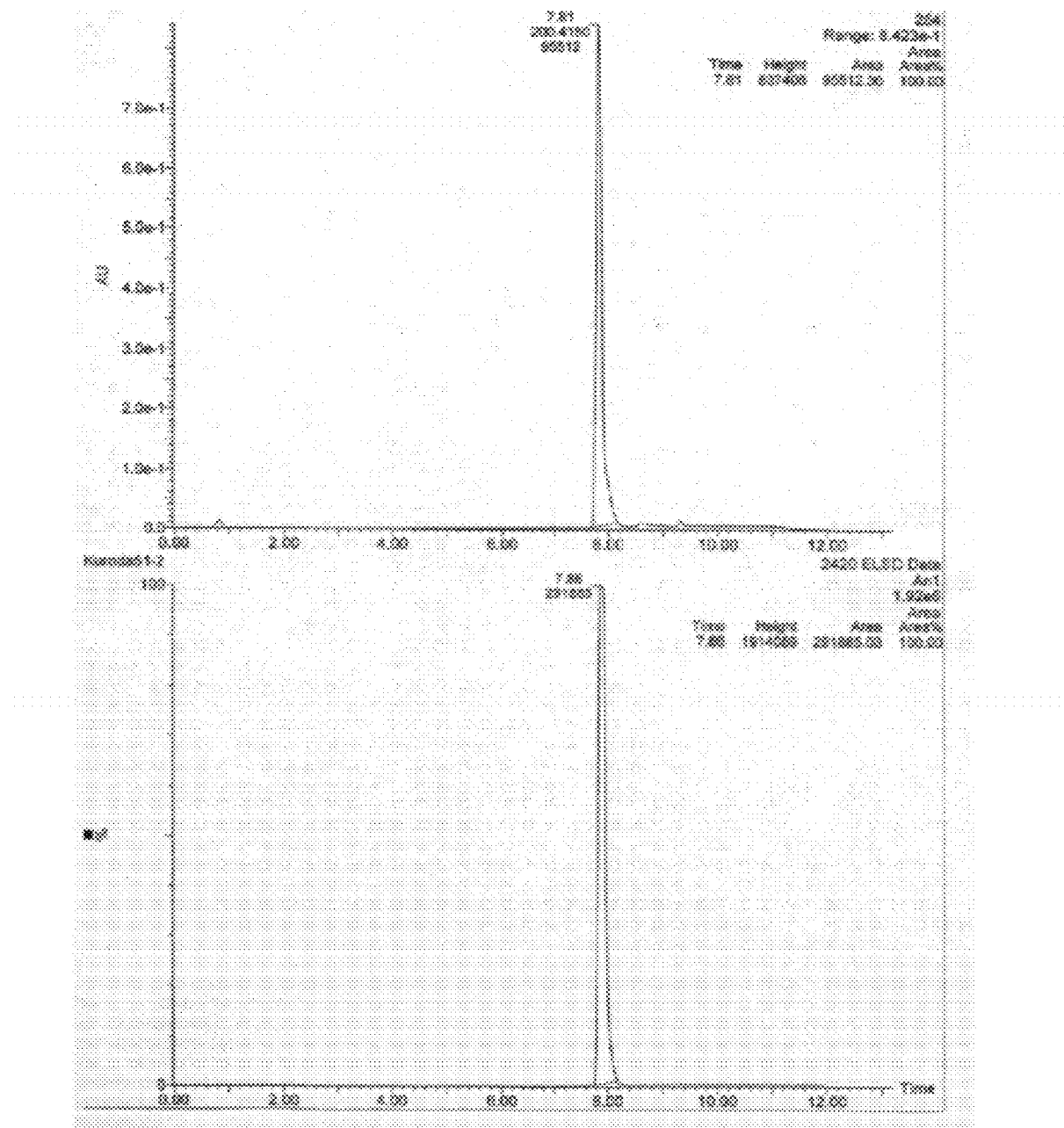
FIG. 4 is a diagram showing the LC-MS spectrum of compound B synthesized in Example 1.

Next, under an argon atmosphere, Compound A (20.0 g, 34.73 mmol, 1.0 equivalent) and 600 ml acetonitrile were placed in a 1.0 L 5 necked flask; methyl iodide (21.6 ml, 347.3 mmoles, 1.0 equivalent) was added with stirring at an internal temperature 23° C.; and the mixture was allowed to gradually cool with stirring. The resultant precipitate was collected by filtration, washed with acetonitrile, and dried at reduced pressure, yielding Compound B, a yellow powder (yield 8.9 g; percent yield 75.9%). The NMR spectrum of the compound B obtained is shown in a FIG. 3. Its LC-MS spectrum is shown in a FIG. 4.

EXAMPLE 2

(Checking Inhibitory Effect on Glutamate Production by Activated Microglia)

Next, Compound A and Compound B were checked as to their inhibitory effect on glutamate production in activated microglia. That is, mouse primary microglia were isolated from primary mixed glial cell cultures, prepared from neonatal C57BL/6 mice brains by the "shaking off" method on the 14th culture day or later (Suzumura, A. et al J. Neuroimmunol. 15, 263-278 1987). Mouse cerebral cortex primary neuronal cells were prepared from the cerebral cortices of C57BL/6J mice at embryonic day 17, and were plated on polyethyleneimine-coated cover glasses, and were used at culture day 10-13 (Takeuchi, H. et al. J. Biol. Chem. 280, 10444-10454, 2005.)

Using the culture system of neuronal cells utilizing a microglia conditioned medium, the neuronal cell damage by activated microglia was analyzed with time by the following methods (Takeuchi, H. et al. J. Biol. Chem. 280, 10444-10454, 2005.) Namely, 1 μg/ml lipopolysaccharide (LPS) and Compound A, Compound B, and carbenoxolone (CBX) at each concentration thereof (1 μM, 10 μM and 100 μM as the final concentrations) were added to a microglia culture (about $5 \times 10^4$ cells/well, a neuronal culture medium, (made by Sumitomo Bakelite Co., Ltd)) followed by incubating under 100% humidity and 5% $CO_2$ for 24 hours. For a control, except for not adding Compound A or Compound B, microglia were incubated in a similar manner (LPS).

Each of the activated microglia conditioned media, 500 μl, 24 hrs after the administration, was added to neuronal cells ($5 \times 10^4$ cells/well) in a 24-well plate, and the neuronal cells were cultured at 37° C. under 100% humidity and 5% $CO_2$. The non-activated microglia conditioned medium was also added to neuronal cells to serve as a control (NT). 24 hours after the start of culturing, the amounts of glutamate and neuronal cell death in the conditioned medium were analyzed.

Determination of glutamate was performed by colorimetry; and neuronal cell death was assessed by the dye-exclusion method with propidium iodide under a fluorescence microscope and the terminal deoxynucleotidyl transferase-mediated UTP end labeling (TUNEL) staining. The results are shown in FIG. 5 and FIG. 6.

Figure 5:
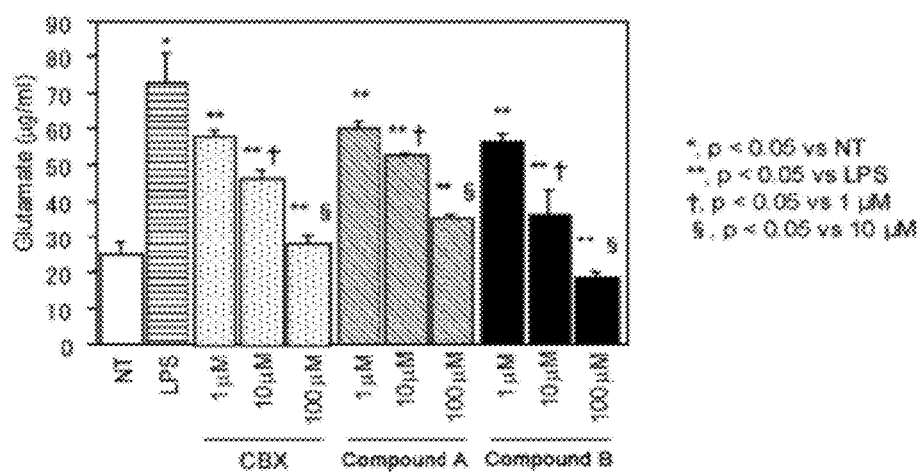
FIG. 5 is a diagram showing the result of determining the glutamate concentration in a neuronal conditioned medium cultured with a microglia conditioned medium. Provided that the * represents $p<0.05$ vs NT; ** $p<0.05$ vs LPS; † $p<0.05$ vs 1 µM; and §$p<0.05$ vs 10 µM. The error bars represent a standard deviation.
Figure 6:
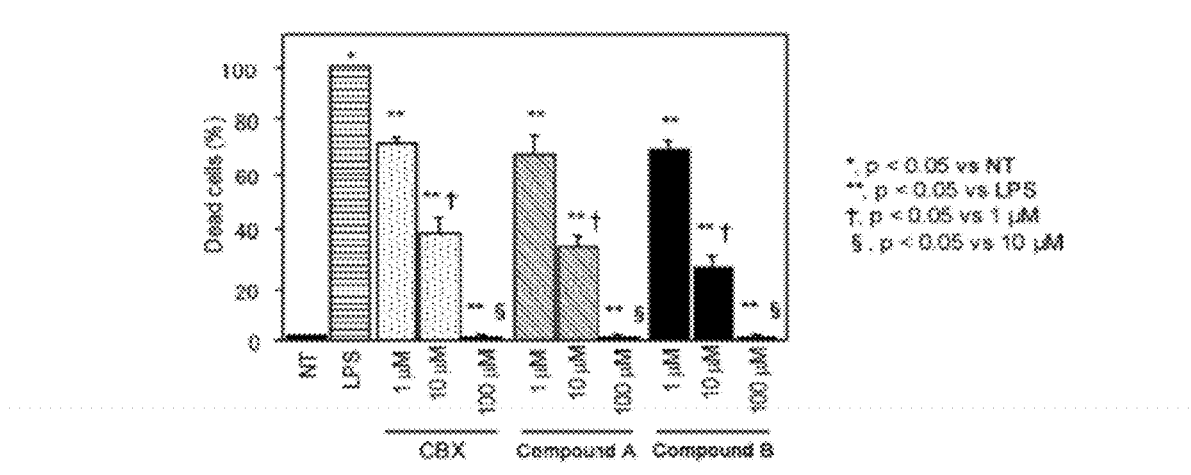
FIG. 6 is diagram showing the result of determining the cell death (%) of the neuronal cells cultured with a microglia-conditioned medium. The * represents $p<0.05$ vs NT; ** $p<0.05$ vs LPS; † $p<0.05$ vs 1 µM; and §$p<0.05$ vs 10 µM. The error bars represent a standard deviation.

As shown in FIG. 5, when the LPS-activated microglia (without addition of Compound B) conditioned medium was added and the neuronal cells were cultured, the glutamate concentration in the conditioned neuron culture medium considerably increased relative to that when co-cultured with non-stimulated microglia, and a glutamate release by the activated microglia was noted. The present inventors already disclosed that when neuronal cells were cultured in an active microglia conditioned medium, the glutamate concentration in the neuronal culture medium depended on the glutamate concentration in the activated microglia conditioned medium (Patent reference 1).

On the other hand, when neuronal cells were cultured by adding a microglia conditioned medium which had been cultured in the co-presence of Compound A, and Compound B, with LPS, the glutamate concentration in the neuron culture media fell in accordance with the concentration of these compounds therein. In particular, it was observed that the activated microglia to which Compound B was added at a 100 μM concentration exhibited glutamate release inhibition comparable to that of the non-stimulated microglia.

The above observation revealed that Compound A and Compound B had inhibited the glutamate release in the LPS-activated microglia. It was also found that Compound B is notably more effective than Compound A.

In addition, as shown in FIG. 6, the cell death of neuronal cells cultured with an added LPS-activated microglia conditioned medium (with no addition of either Compound A or Compound B) substantially increased (about 100%) in comparison to the case (about 0%) of co-culturing with non-stimulated microglia, thereby showing that an activated microglia medium induces neuronal cell death. As described above, this is disclosed in Patent reference 1.

On the other hand, when administered with microglia conditioned medium along with the addition of Compound A and Compound B respectively and with LPS, neuronal cell death (%) was inhibited in a concentration-dependent manner of Compound A or Compound B.

Accordingly, it was revealed that Compound A and Compound B inhibit the glutamate release in the LPS-activated microglia, thereby inhibiting neuronal cell death. In particular, Compound B was found to have a high glutamate release inhibitory effect.

EXAMPLE 3

Checking the Survival Extension Effect in an ALS Model Mouse)
The assessment of drug efficacy was conducted using, as an animal model of neurodegenerative diseases, the human superoxide dismutase 1 (SOD1) G93A mutant transgenic mouse, which is widely used as a model of amyotrophic lateral sclerosis (ALS). Said transgenic mice were procured from Jackson Laboratory, USA.

Starting at 6-7-weeks of age, which is considered to be an early ALS onset period, they were intraperitoneally administered with 20 mg/kg body weight of Compound B, which is a novel gap junction inhibitor, CBX, or the same volume of physiological saline (PBS group) 3 times a week. The survival analysis was performed using the Kaplan-Meier method. The results are shown in FIG. 7.

Figure 7:
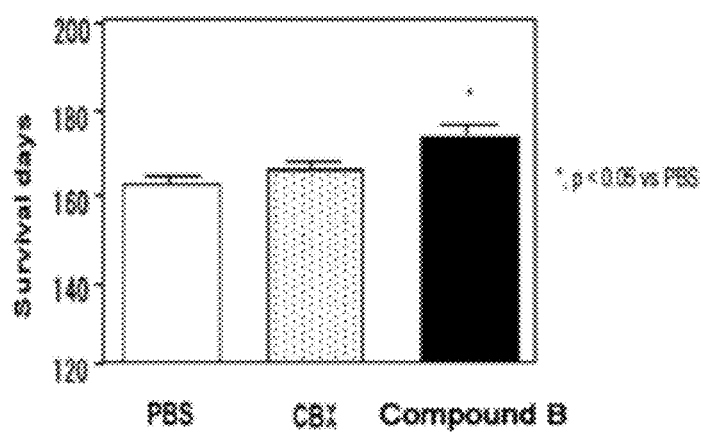
FIG. 7 is a diagram showing the result of survival extension by an intraperitoneal injection of Compound B into ALS model mice. * represents $p<0.0002$ vs PBS.

As shown in a FIG. 7, the Compound B administered group showed on average an effect of extending survival by about 14 days (*, $p<0.0002$ vs PBS). The 14 day survival extension was a very good survival extension effect for this model mouse. This finding shows that Compound B reaches the central nervous system and manifests its efficacy.

EXAMPLE 4

(Checking the Survival Extension Effect in an Acute-Onset ALS Model Mouse)
The assessment of drug efficacy at different Compound B concentrations was conducted using, as an animal model of neurodegenerative diseases, a human superoxide dismutase 1 (SOD1) (G93A) mutant transgenic mouse, which is widely used as an acute-onset model of amyotrophic lateral sclerosis (ALS).

Starting at 7-8-weeks of age, which is considered to be an early ALS onset period, they were intraperitoneally administered with 5, 10, and 20 mg/kg body weight of the novel gap junction inhibitor (Compound B) or the same volume of physiological saline (PBS group) 3 times a week. The survival analysis was performed using the Kaplan-Meier method. The results are shown in FIG. 8.

Figure 8A:
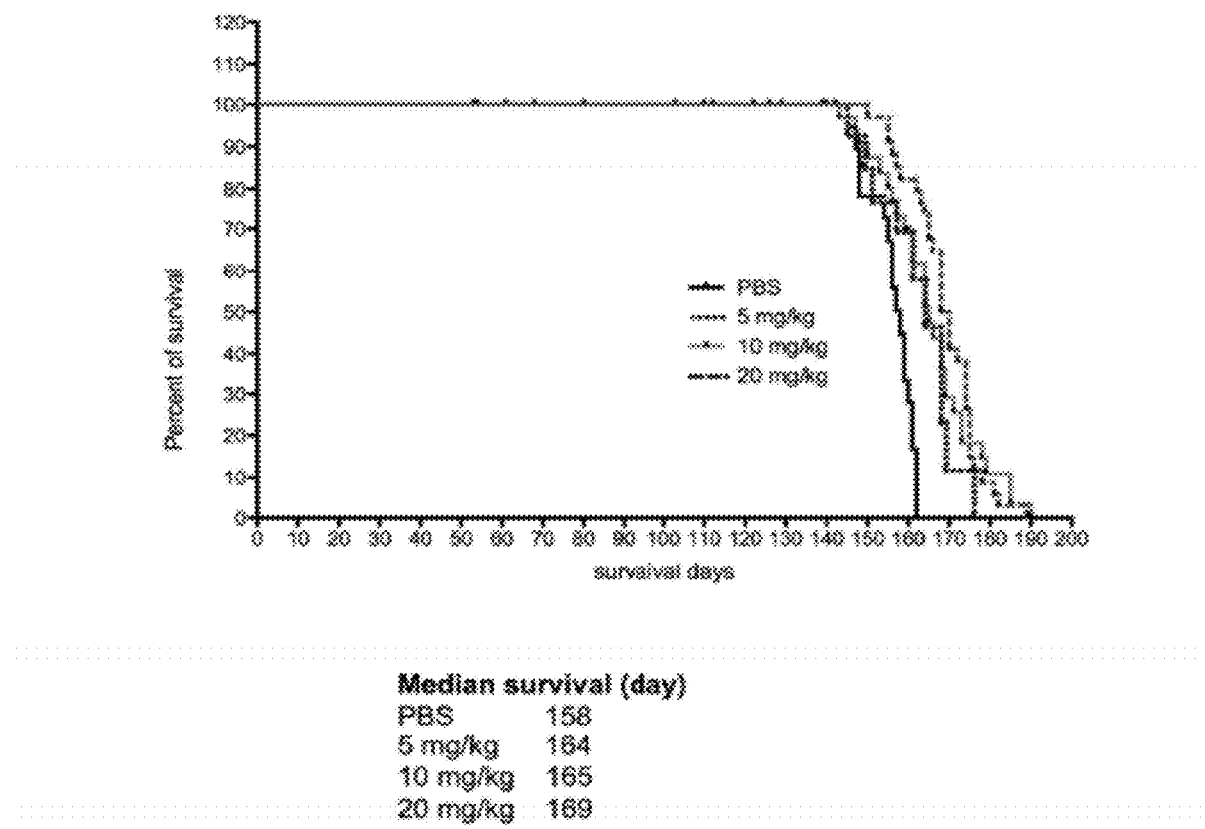
FIG. 8 is a diagram showing the result of survival extension effect of ALS acute-onset model mice in accordance with the difference in the amounts of Compound B administered. The * represents $p<0.0001$ vs PBS.
Figure 8B:
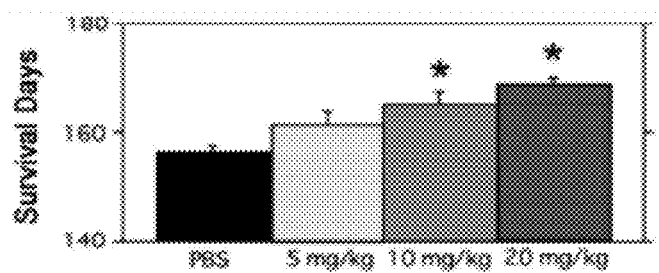

As shown in a FIG. 8, the 20 mg/kg Compound B administered group showed on average an effect of extending survival by about 2 weeks (*, $p<0.0001$ vs PBS). Such a survival extension is considered to be a very good survival extension effect for this model mouse. The error bars in the Figure indicate a standard deviation.

EXAMPLE 5

(Checking the Survival Extension Effect in a Late-Onset ALS Model Mouse)
The assessment of drug efficacy of Compound B was conducted similarly to Example 4 using, as an animal model of neurodegenerative diseases, the human SOD1 G37R mutant transgenic mouse, which is widely used as a late-onset model of amyotrophic lateral sclerosis (ALS).

Starting at 7 months of age, which is considered to be an early onset period, they were intraperitoneally administered with 5, 10, and 20 mg/kg body weight of the novel gap junction inhibitor (Compound B) or the same volume of physiological saline (PBS group) 3 times a week. The survival analysis was performed using the Kaplan-Meier method. The results are shown in FIG. 9.

Figure 9A:
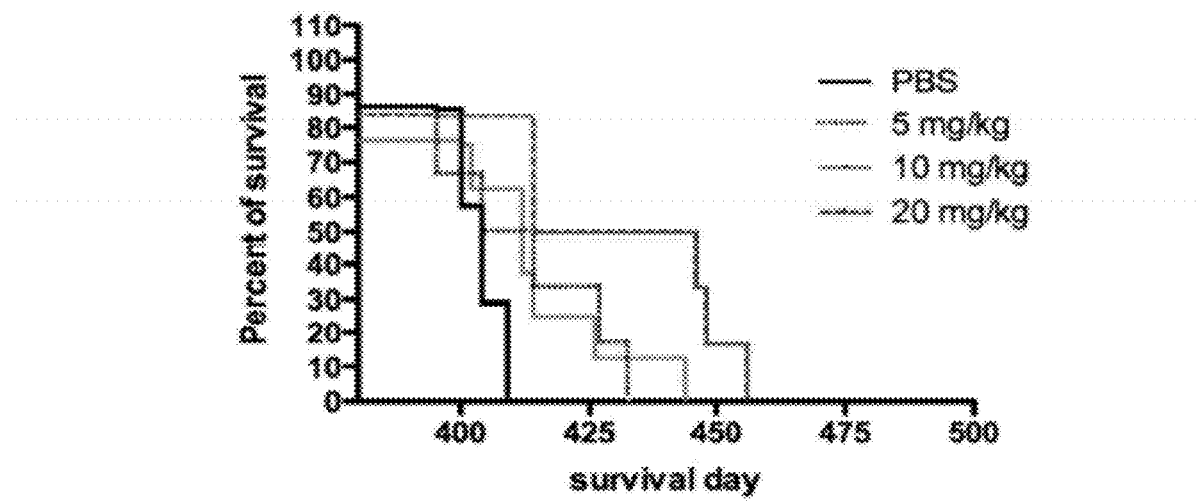
FIG. 9 is a diagram showing the result of survival extension of ALS late-onset model mice in accordance with the difference in the amounts of Compound B administered. The * represents $p<0.05$ vs PBS.
Figure 9B:
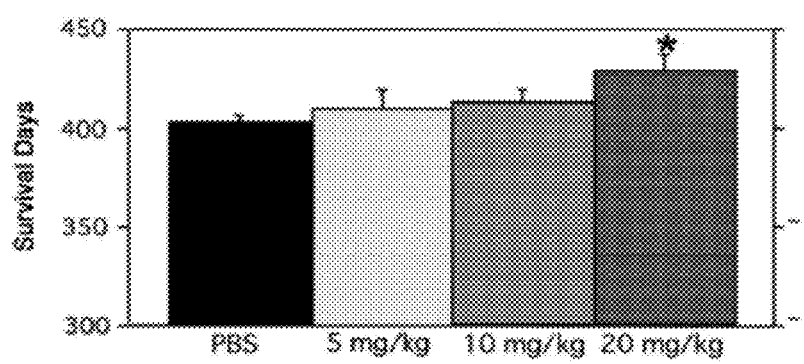

As shown in a FIG. 9, the 20 mg/kg Compound B administered group showed on average an effect of extending survival by about one month (*, $p<0.005$ vs PBS). Such a survival extension is considered to be a very good survival extension effect for this model mouse. The error bars in the Figure indicate a standard deviation.

EXAMPLE 6

(Checking the Survival Extension Effect in an Alzheimer's Disease Model Mouse)
The assessment of drug efficacy of Compound B was conducted using, as an animal model of neurodegenerative diseases, the human amyloid precursor protein/human presenilin-1 (APP/PS1) mutant double transgenic mouse, which is widely used as an Alzheimer's disease model mouse.

Starting at 9 months of age, which is considered to be an intermediate onset period, they were intraperitoneally administered with 10 and 20 mg/kg body weight of Compound B or the same volume of physiological saline (PBS group) 3 times a week. The control group was a wild type mouse (G57BL/6J) of the same age. Behavioral analysis was performed using the following three types of behavior experiments.

Figure 10:
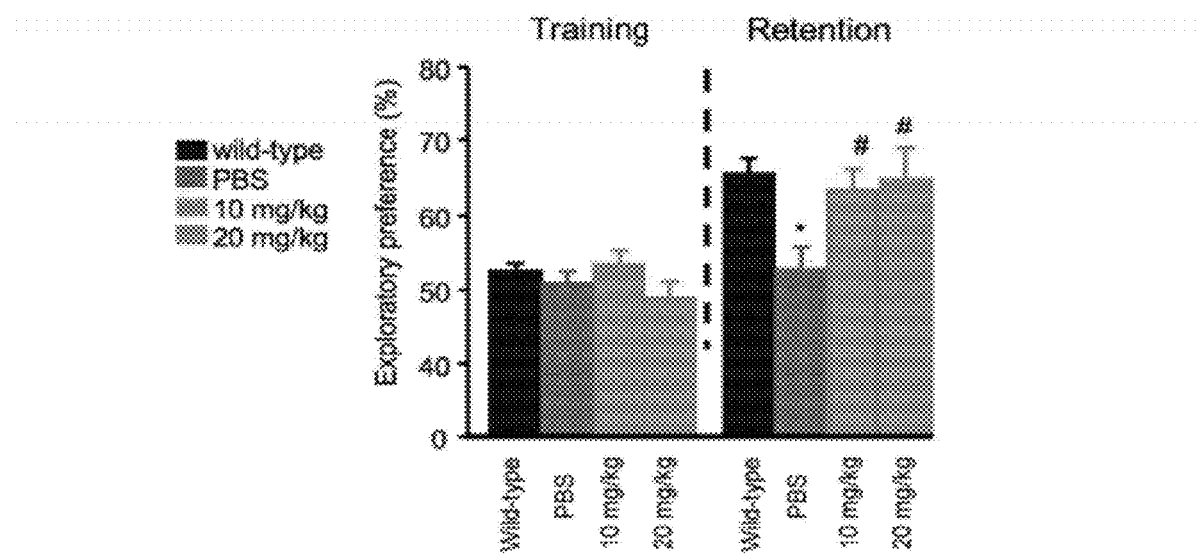
FIG. 10 is a diagram showing the memory disorder improvement effect of Compound B on Alzheimer's disease model mice, an increase in a novel object substance exploratory preference. The * represents $p<0.05$ vs wildness type; # $p<0.05$ vs PBS.

(1) Novel object exploration test: After the mice were habituated for 3 days (10 minutes/day) in an acrylic experiment apparatus, they were subjected to training. The raining consisted of placing two different objects in the apparatus and they were allowed to freely explore for 10 minutes. 24 hours after the training, Retention was carried out. The Retention consisted of replacing one of the two objects which had been placed in the apparatus during the training with a novel object and allowing the mice to freely explore for 5 minutes. The times spent exploring (touching, sniffing behavior and the like) the two objects were determined respectively. The ratio of the time spent exploring the novel object, in the Retention session, over the total time spent exploring both objects, was defined as an exploratory preference, as a cognitive memory index. (Mouri et al., FASEB J. 21, 2135-2148, 2007; Mizoguchii et al., Psychopharmacology (Berl). 196, 233-241, and 2008). The results are shown in FIG. 10.

The APP/PS1 mice which were administered with none of the novel gap junction inhibitor (Compound B) had a novel object exploratory preference significantly lower than the wild type mice. The Compound B administered group had an exploratory preference significantly greater than the PBS administered group. The * in the Figure indicates $P<0.05$ vs wild type; $p<0.05$ vs PBS, respectively.

Figure 11:
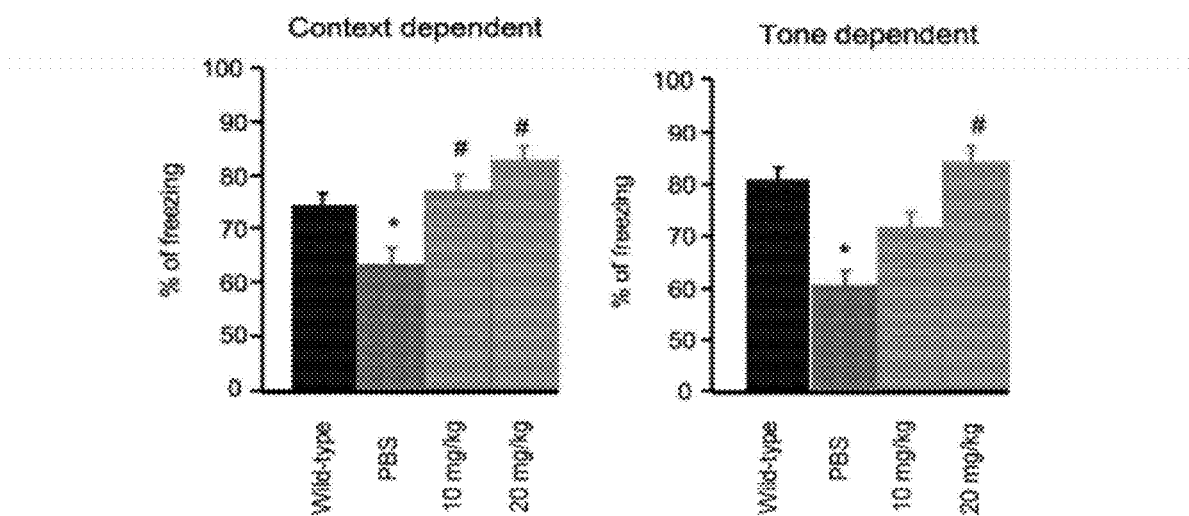
FIG. 11 is a diagram showing the memory disorder improvement effect of Compound B of Alzheimer's disease model mice, a moderation in contextual dependency and tone stimulus dependency. The * represents $p<0.05$ vs wildness type; #$p<0.05$ vs PBS.

(2) Fear conditioned learning test: Associative learning was assessed using a fear conditioned learning test (Mouri et al., FASEB J. 21, 2135-2148, 2007; Nagai et al., FASEB J. 17, 50-52, and 2003). The mice were placed in a transparent acrylic cage with a stainless steel grid installed therein and were subjected to a 20 second tone stimulus (80 dB), and then further to an electric stimulus (0.6 mA). A set of this combination stimulus was repeated 4 times with 15 second intervals, thereby causing fear conditioning. A contextual dependency test and a tone stimulus dependency test were carried out 24 hours after the fear conditioning. For the former, mice were placed in the white acrylic cage with a grid where the fear conditioning took place to determine their freezing behavior for two minutes under a context of giving no tone and no electric stimuli. For the latter, mice were placed in a black acrylic cage having wood chips on the floor thereof, to determine their freezing behavior for 1 minute when given a continuous tone stimulus. The results were expressed respectively in terms of a percentage (%) of the freezing behavior time relative to the total time for determination. The results are shown in FIG. 11.

APP/PS1 mice with no administered compound B showed a significant reduction in freezing behavior time compared with the wild type in contextual dependency and tone stimulus dependency tests. The Compound B administered group significantly moderated the observed reduction in freezing behavior time in the contextual dependency test in the case of APP/PS1 mice with no administered compound B. Also in the tone stimulus dependency test, the Compound B administered group showed a dose-dependent increase in the freezing behavior time such that, the 20 mg/kg administered group showed a significant moderation effect. The * in the Figure represents $p<0.05$ vs the wild type; represents $p<0.05$ vs PBS, respectively.

Figure 12A:
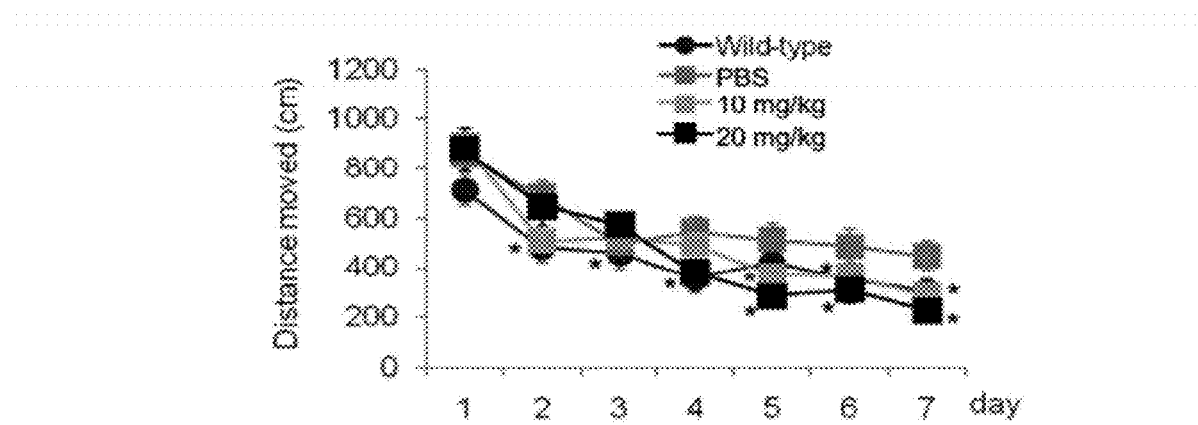
FIG. 12 is a diagram showing the memory disorder improvement effect of Compound B of Alzheimer's disease model mice, an improvement of space cognitive memory. The * represents \$p<0.05$ vs wildness type; #$p<0.05$ vs PBS.
Figure 12B:
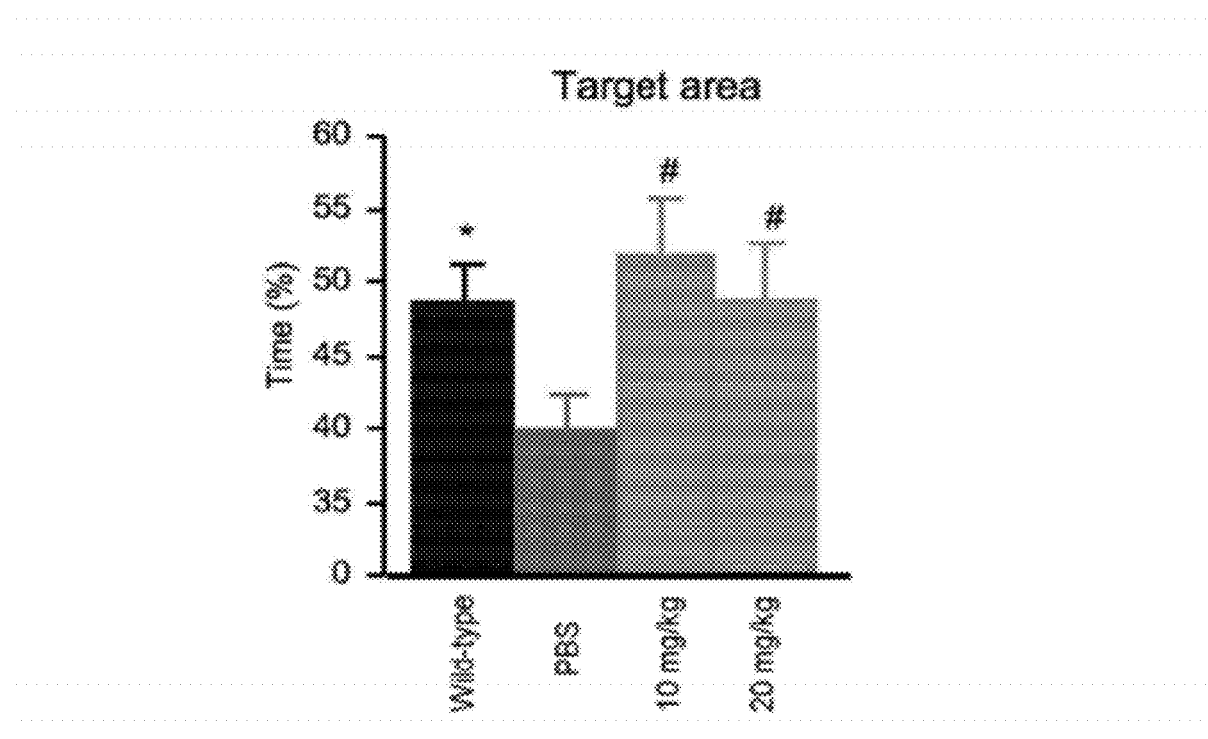

(3) Morris water maze test: Spatial recognition memory was evaluated using the Morris water maze test (Mouri et al. and FASEB J. 21 2135-2148 2007; Miyamoto et al; J. Neurosci. 25, 1826-1835 2005). A 60 second trial was conducted 3 times a day to determine the swimming time (escape latency) and swimming distance (distance moved) from a different start position to a fixed platform. This was performed for seven days in row; on the eighth day, a probe test was performed with the platform removed. The Probe test involved dividing the water maze into 4 regions consisting of Target (Platform), Right, Opposite, and Left and determining the ratios of the regions in which they swam over 60 seconds. The items to be determined were determined using the SMART system (Panlab, Barcelona, Spain). The results are shown in FIG. 12.

The distance swum by the APP/PS1 mice which were not administered with Compound B increased significantly relative to that of the wild type mice, with their exploration of the target area in a Probe test also standing at 39.6±2.3%. On the other hand, although the distance swum by the 10 mg/kg Compound B administered group on training day 1 was about the same as that of the PBS administered group, it fell significantly on training day 5-7. Similarly the 20 mg/kg Compound B administered group on training day 4-7 showed a significant reduction in the swimming time and in the distance swum. In addition the groups administered with Compound B, a novel gap junction inhibitor, showed a significantly increased swimming time in the target region. The * in the Figure represents $p<0.05$ vs PBS; ** $p<0.05$ vs Wild type; and $p<0.05$ vs PBS, respectively.

Thus, significant improvement effects in memory disorders were shown in all of the three types of behavioral analyses conducted in Example 6.

EXAMPLE 7

(Hippocampal Glutamate Concentration Determination)

Figure 13:
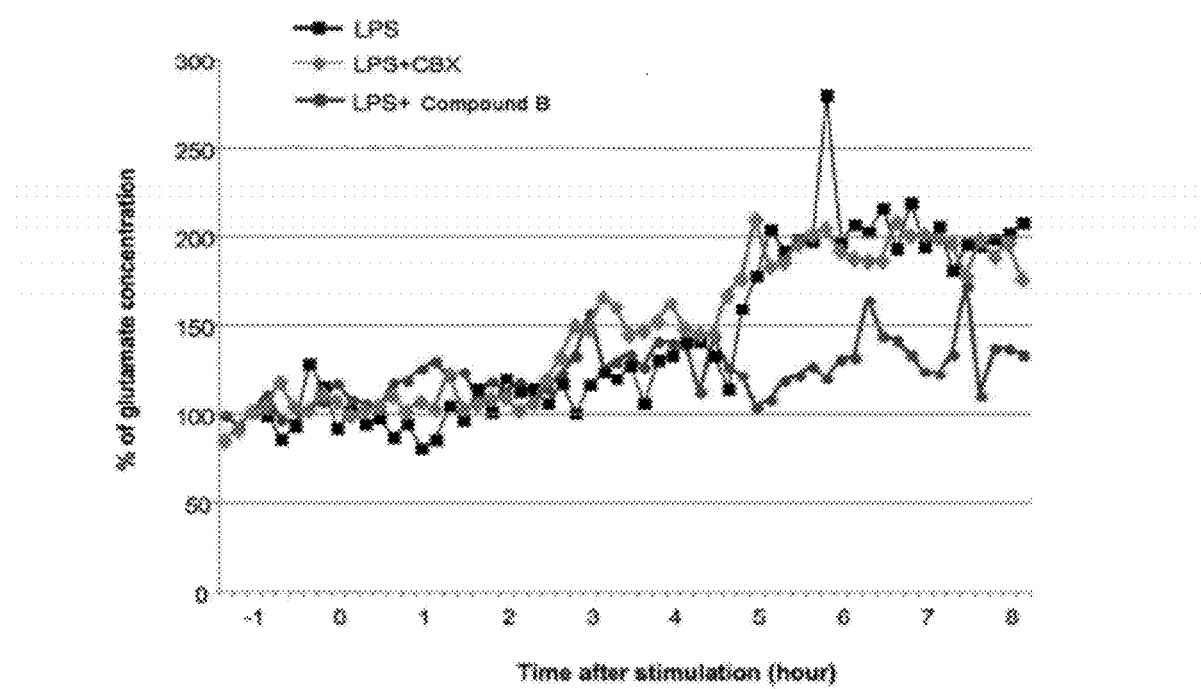
FIG. 13 is a diagram showing the time course change in the hippocampal glutamate concentration in C57BL/6J mice.

A microdialysis catheter was indwelled stereotaxically (in place) into the hippocampus of C57BL/6J mice (8 weeks of age, female, n=5 to 7). After settlement for 48 hours, the determination of the hippocampal glutamate with time was started using high-speed liquid chromatography (HPLC, HITEC-500 GAD, made by Eicom Corp. A stimulus was given by administering 10 μg/2 μl of lipopolysaccharide (LPS) through said catheter, along with an intraperitoneal injection of 20 mg/kg body weight CBX or Compound B simultaneously with the LPS stimulus administration, for a pharmacological efficacy assessment. The hippocampal glutamate concentration was quantified as a % value relative to the average value thereof from 120 minutes to 60 minutes before the stimulus was given to each individual. The results are shown in FIG. 13.

Groups administered with neither Compound B nor CBX showed a notable increase in the hippocampal glutamate concentration from about 4 hours after the LPS stimulus was given, reaching a plateau after 5 hours. Also, no inhibitory effect on the increase in the hippocampal glutamate was observed in the group administered with CBX. On the other hand, the group administered with Compound B showed a significant inhibitory effect on the rise in hippocampal glutamate ($p<0.05$).

EXAMPLE 8

(Acute Toxicity of CBX and Compound B)

Acute toxicity was studied with an intraperitoneal injection of 200 mg/body weight, kg (10-fold) and 1000 mg/body weight, kg (50-fold) of CBX or Compound B. As a result, all mice among the CBX administered group died within 24 hours, but there were no death cases among the group administered with Compound B.

The results from these Examples 7 and 8 demonstrate the excellent delivery of the drug to the central nervous system in an in vivo administration of the novel gap junction inhibitor related to the present invention and its effect of reducing systemic side effects.

What is claimed is:

1. A glycyrrhetinic acid derivative represented by the following general formula (1) and pharmaceutically acceptable salts thereof; (wherein (in the formula, ring A represents a heterocyclic ring which may also have a substituent group in addition to R1; R1 a linear or branched alkyl group having 1 to 6 carbon atoms; R2 a hydroxyl or carbonyl(O=) group; R3 a hydrogen atom, a hydroxyl group or a linear or branched alkyl group having 1 to 4 carbon atoms; R4 a hydrogen atom, a hydroxyl group, or a linear or branched alkyl group having 1 to 4 carbon atoms; R5 a hydrogen atom, a hydroxyl, a carbonyl group (O=) or a linear or branched alkyl group having 1 to 4 carbon atoms; R6 a hydrogen atom, a hydroxyl, a carbonyl group (O=) or a linear or branched alkyl group having 1 to 4 carbon atoms, or a halogen atom; R7 a hydrogen atom or a hydroxyl group; and $X^-$ represents an anion)

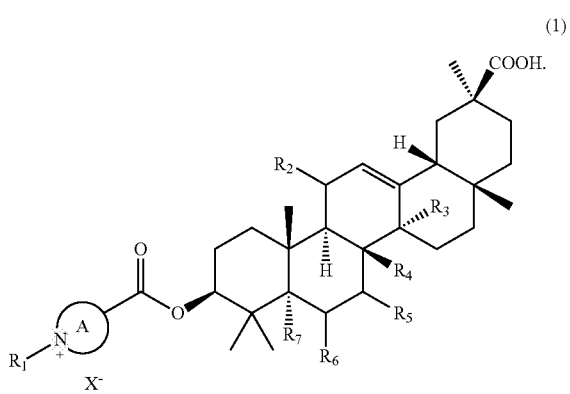

(1)

2. The glycyrrhetinic acid derivatives as set forth in claim 1 wherein in said general formula (1), Ring A is one of pyridine, quinoline, isoquinoline, imidazole, oxazole, thiazole, benzoxazole, 2,1-benzisooxazole, benzthiazole or 2,1-benzisothiazole.

3. The glycyrrhetinic acid derivatives as set forth in claim 2 wherein in said general formula (1), Ring A has only R1 as a substituent group.

4. The glycyrrhetinic acid derivatives as set forth in claim 3 wherein in said general formula (1), R1 represents a methyl group.

5. The glycyrrhetinic acid derivatives as set forth in claim 4 wherein in said general formula (1), Ring A is pyridine.

6. The glycyrrhetinic acid derivative as set forth in claim 5 represented by the following
Chemical formula:

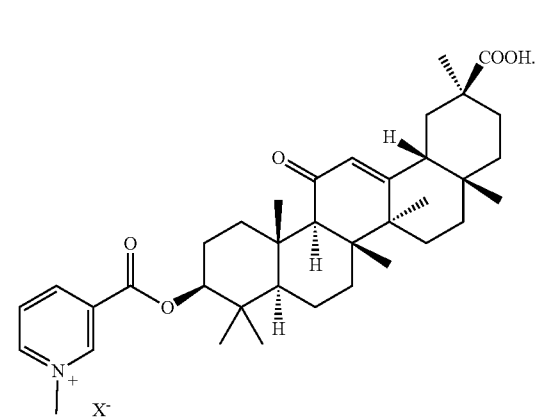

(3)

7. A pharmaceutical composition containing as an active ingredient the glycyrrhetinic acid derivative as set forth in any one of claims 1 to 6.

8. The pharmaceutical composition as set forth in claim 7 wherein said composition is used for treating a glutamate-induced excitotoxic neurodegenerative disease wherein the disease comprises Alzheimer's disease, Parkinson's disease, or amyotrophic lateral sclerosis.

9. A method for treating a mammal afflicted with a glutamate-induced excitotoxic neurodegenerative disease wherein the disease comprises Alzheimer's disease, Parkinson's disease, or amyotrophic lateral sclerosis, said method comprising:

the step of making available a therapeutically effective amount of a glycyrrhetinic acid derivative represented by general formula (1) or (2) and pharmaceutically acceptable salts thereof

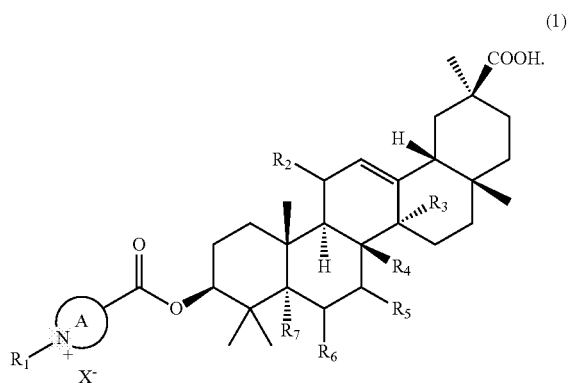

(1)

10. The method as set forth in claim 9 wherein the mammal is a human.

11. The method as set forth in claim 9 wherein said step of administering is performed orally.

12. The method as set forth in claim 9 wherein the Ring A in said general formula (1) or (2), Ring A is one of pyridine, quinoline, isoquinoline, imidazole, oxazole, thiazole, benzoxazole, 2,1-benzisooxazole, benzthiazole or 2,1-benzisothiazole.

13. The method as set forth in claim 12 wherein Ring A said general formula (1) or (2) has only R1 as a substituent group thereof.

14. The method as set forth in claim 13 wherein R1 in said general formula (1) or (2) represents a methyl group.

15. The method as set forth in claim 14 wherein Ring A in said general formula (1) or (2) is pyridine.

16. The method as set forth in claim 15 wherein the compound represented by the following chemical formula as a glycyrrhetinic acid derivative and a pharmaceutically acceptable salt thereof

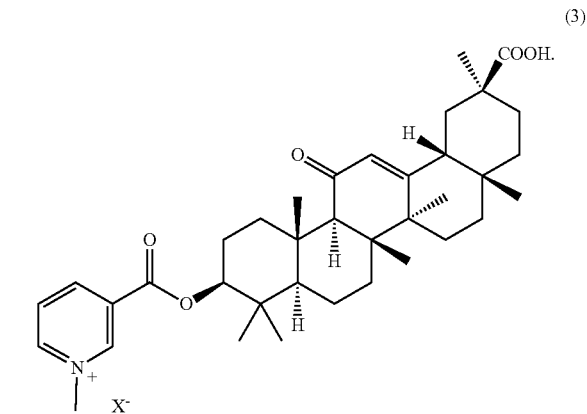

(3)

(2)

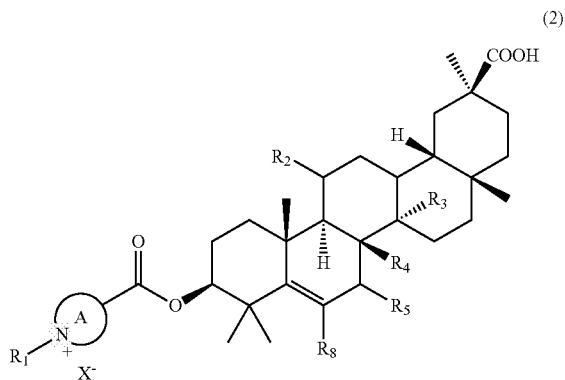

(wherein
in the formula, ring A represents a heterocyclic ring which may also have a substituent group in addition to R1; R1 a linear or branched alkyl group having 1 to 6 carbon atoms; R2 a hydroxyl or carbonyl (O═) group; R3 a hydrogen atom, a hydroxyl group or a linear or branched alkyl group having 1 to 4 carbon atoms; R4 a hydrogen atom, a hydroxyl group, or a linear or branched alkyl group having 1 to 4 carbon atoms; R5 a hydrogen atom, a hydroxyl, a carbonyl group (O═) or a linear or branched alkyl group having 1 to 4 carbon atoms; R6 a hydrogen atom, a hydroxyl, a carbonyl group (O═) or a linear or branched alkyl group having 1 to 4 carbon atoms or a halogen atom; R7 a hydrogen atom or a hydroxyl group; R8 a hydrogen atom, a hydroxyl group or a halogen atom; and X⁻ represents an anion):
and the step of administering to said mammal a therapeutically effective amount of said available glycyrrhetinic acid derivatives and pharmaceutically acceptable salts thereof.

17. A glycyrrhetinic acid derivative represented by the following general formula (2) and pharmaceutically acceptable salts thereof; (wherein
(in the formula, ring A represents a heterocyclic ring which may also have a substituent group in addition to R1; R1 a linear or branched alkyl group having 1 to 6 carbon atoms; R2 a hydroxyl or carbonyl(O═) group; R3 a hydrogen atom, a hydroxyl group or a linear or branched alkyl group having 1 to 4 carbon atoms; R4 a hydrogen atom, a hydroxyl group, or a linear or branched alkyl group having 1 to 4 carbon atoms; R5 a hydrogen atom, a hydroxyl, a carbonyl group (O═) or a linear or branched alkyl group having 1 to 4 carbon atoms; R8 a hydrogen atom, a hydroxyl group or a halogen atom; and X⁻ represents an anion)

(2)

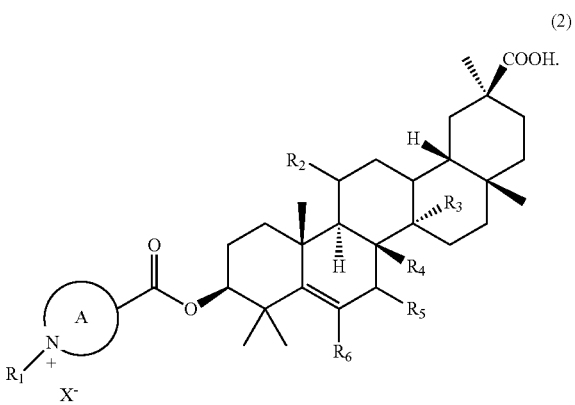

18. The glycyrrhetinic acid derivatives as set forth in claim 17 wherein in said general formula (2), Ring A is one of pyridine, quinoline, isoquinoline, imidazole, oxazole, thiazole, benzoxazole, 2,1-benzisooxazole, benzthiazole or 2,1-benzisothiazole.

19. The glycyrrhetinic acid derivatives as set forth in claim 18 wherein in said general formula (2), Ring A has only R1 as a substituent group.

20. The glycyrrhetinic acid derivatives as set forth in claim 19 wherein in said general formula (2), R1 represents a methyl group.

21. The glycyrrhetinic acid derivatives as set forth in claim 20 wherein in said general formula (2), Ring A is pyridine.

22. A pharmaceutical composition containing as an active ingredient the glycyrrhetinic acid derivative as set forth in any one of claims 17 to 21.

23. The pharmaceutical composition as set forth in claim 22 wherein said composition is used for treating a glutamate-induced excitotoxic neurodegenerative disease wherein the disease comprises Alzheimer's disease, Parkinson's disease, or amyotrophic lateral sclerosis.

* * * * *